(12) United States Patent
Souaida

(10) Patent No.: US 10,463,393 B2
(45) Date of Patent: Nov. 5, 2019

(54) CIRCUMCISION DEVICE

(71) Applicant: Mamdouh Youssef Soliman Souaida, Gisza (EG)

(72) Inventor: Mamdouh Youssef Soliman Souaida, Gisza (EG)

( * ) Notice: Subject to any disclaimer, the term of this patent is extended or adjusted under 35 U.S.C. 154(b) by 60 days.

(21) Appl. No.: 15/503,268

(22) PCT Filed: Aug. 3, 2015

(86) PCT No.: PCT/EG2015/000036
§ 371 (c)(1),
(2) Date: Feb. 10, 2017

(87) PCT Pub. No.: WO2016/023564
PCT Pub. Date: Feb. 18, 2016

(65) Prior Publication Data
US 2018/0206876 A1 Jul. 26, 2018

(30) Foreign Application Priority Data
Aug. 11, 2014 (EG) ................. 2014081290

(51) Int. Cl.
*A61B 17/326* (2006.01)
*A61B 17/00* (2006.01)

(52) U.S. Cl.
CPC .... *A61B 17/326* (2013.01); *A61B 2017/0023* (2013.01); *A61B 2017/0046* (2013.01); *A61B 2017/00526* (2013.01)

(58) Field of Classification Search
CPC .......... A61B 17/326; A61B 2017/0023; A61B 2017/0046; A61B 2017/00526
See application file for complete search history.

(56) References Cited

U.S. PATENT DOCUMENTS 3,056,407 A * 10/1962 Kariher ................ A61B 17/326
606/118
7,303,567 B1 12/2007 Smith
2007/0060928 A1 * 3/2007 Dave .................... A61B 17/326
606/118

FOREIGN PATENT DOCUMENTS

EG 17446 A 3/1989
GB 837252 A 6/1960

OTHER PUBLICATIONS

International Search Report dated Sep. 14, 2015 for PCT Application No. PCT/EG2015/000036.

* cited by examiner

*Primary Examiner* — George J Ulsh
(74) *Attorney, Agent, or Firm* — Moser Taboada

(57) ABSTRACT

A circumcision device comprises a hollow bell-shaped body, a semi-conical part, and a handle. The body comprises an open anterior end, an open posterior end, a circumferential flange proximal to the open anterior end on an exterior surface of the body. The semi-conical part comprises an open anterior end and an open posterior end. The open posterior end extends from the circumferential flange. The open anterior end of the semi-conical part prevents slippage of the circumcision device to a shaft of a penis on which the circumcision device is configured to be mounted, when the circumcision device is mounted on the penis. The handle has an inverted Y-shape comprising two forked legs, each of the two forked legs coupled to a periphery of the open anterior end of the semi-conical part, the coupling forming a junction. The junction is formed structurally weak to facilitate detaching the handle from the semi-conical part.

7 Claims, 4 Drawing Sheets

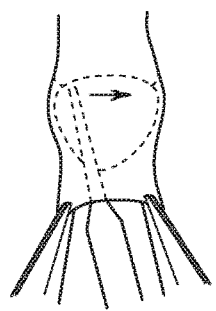
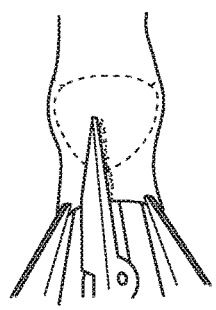
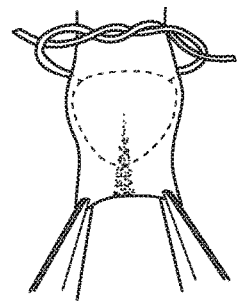
FIG. 7     FIG. 8     FIG. 9
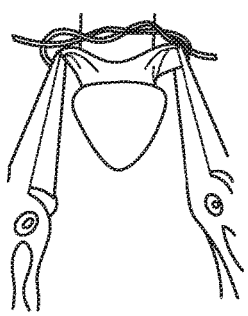
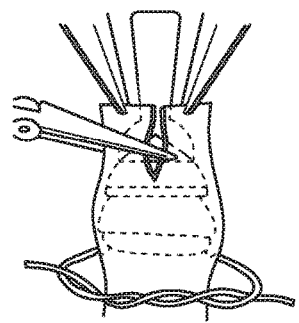
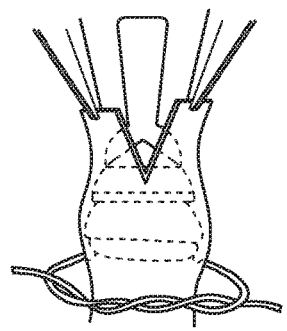
FIG. 10     FIG. 11     FIG. 12
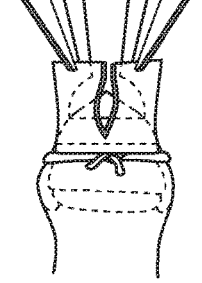
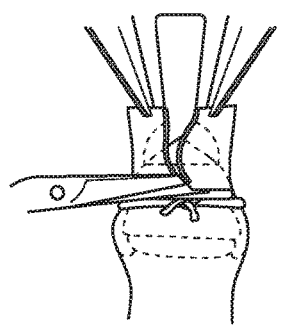
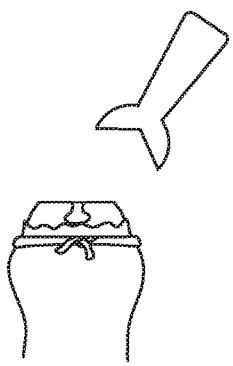
FIG. 13     FIG. 14     FIG. 15

CIRCUMCISION DEVICE

TECHNICAL FIELD

This invention relates to a surgical device used in performing circumcisions, and, more particularly, to a circumcision ring which permits the performance of a circumcision by ligation and having a semi conical hollow body at the anterior part of the ring to avoid its slipping through the shaft of penis leading to complications seen in related devices.

BACKGROUND OF THE INVENTION

Circumcisions have been performed for many years using a circumcision device of the type having a tapered, bell-shaped ring adapted to fit over the glans of a penis and under the foreskin. The ring has an anterior end and a posterior end which is larger than the anterior end. A handle, as connected to the anterior end, is grasped by the surgeon in properly positioning the ring over the glans. A string or ligature is subsequently tied around the foreskin so as to compress the foreskin into a groove that circumferentially extends around the exterior of the ring. The handle is then broken off and detached from the ring by means of a structurally weakened junction with the anterior end of the ring. After about 3-8 days, foreskin under and distal to the ligature dies, and the ring falls off the penis to complete the circumcision.

In many cases, after the circumcision device is positioned and prepared for circumcision with the ring received over the glans, factors such as body movement. penile erection, tissue changes, or simply a missized ring can cause the glans to slip partially or even entirely through the ring and its smaller anterior end so as to excessively protrude therefrom and cause the ring to constrict the penis. As a result, the penis swells and the ring may not fall off the penis after the normal period as intended. In addition to possible infection or damage to the urethra and sloughing of the skin. failure of the ring to fall off the penis necessitates manual removal of the ring, which can require cutting the ring off the penis in an undesirable and delicate procedure.

In a recent device having the same mechanism of circumcision a bridge extending over the anterior opening of the ring and fixedly connected to the anterior end at circumferentially spaced points thereof, and a handle fixedly but frangibly connected to the bridge. After finishing the operation, the handle is detached from the bridge, which remains connected to the anterior end of the ring. The bridge can then act as an obstruction to the glans of the penis to thereby limit protrusion of the glans from the anterior end of the ring. This obstruction of the glans of penis by the bridge although will prevent slipping of the ring to the shaft of the penis but partial protrusion of the glans against the bridge will obstruct the urethral opening due to direct compression leading to urinary obstruction. As a result of the partial protrusion of the glans it will be constricted within the outer opening and swells and the ring may not fall off the penis after the normal period as intended.

A circumcision device was invented by me (FIG. 1) at 1988/17446 in which a semi conical hollow part 15 was added at the anterior part of the bell shaped hollow body 13 with a circumferential flange 17 anteriorly connected to the body posteriorly with a circumferential groove 18. The posterior part of the body was opened and defined as posterior opening 19. The interior surface of the body and the semi conical part was tapering and smooth to accommodate the glans shape. The detachable crescentic handle 14 was connected to the anterior part of the flange away from the semi conical part. The semi conical hollow part had an anterior opening and a smaller opening at its base 16 when connecting to the anterior part of the ring to get rid of collected urine. The semi conical part was added to prevent slipping of the ring above the penile shaft. Two problems encountered in this device, firstly urine will be accumulated by surface tension since the area between the glans and the interior surface of the semi conical part was very small so, the small opening at the base done 16 was not enough to get rid of all the urine which will become a good media for growth of bacteria. Secondly, during its manufacturing using plastic molding injection from the top of the handle, the liquid plastic not equally and satisfactory distributed through the semi conical part and rest of the body.

DISCLOSURE OF THE INVENTION

It is, therefore, an object of the invention to provide a circumcision device (FIG. 2 & FIG. 3). of the type having a ring with a hollow bell shaped, a hollow semi conical part, and handle, which prevents slipping of the glans from the ring that can lead to the complications described above. It is applicable and can be made of hard transparent plastic by a method of injecting plastic mold and can be formed sterile and disposable for single use to prevent infection. The material of plastic must be safe and not irritating to the skin of enfants.

The above object is realized by a circumcision device comprising: a ring bell shaped body 25 having a tapered interior surface, an anterior end, and anterior opening which is connected to the semi conical hollow object 21 with an open posterior end 26. A posterior opening defined by the interior surface at the posterior end which is larger than the anterior opening, a longitudinal axis 3 extending between and through the anterior and posterior openings. A semi conical object 21 extending over the anterior opening and fixedly connected to the anterior end at a circumferential flange 23 thereof on exterior surface, and a groove 24 circumferentially defined around the exterior surface adjacent to the anterior end between the circumferential flange and the rest of the body, and a handle 20 is in the form of inverted Y-shape, 2 mm thick, connected by both legs to the top of the anterior edge of the semi conical part. The handle extending longitudinally and outwardly from the junction and being structurally weaker at and adjacent to the junction than any other portion of the handle to thereby make the handle readily breakable and detachable from the edge of the semi conical part at the junction. The presence of the handle attached anteriorly to the top of the semi conical object (not to the top of the body in some devices or to a bridge in others or away from the semi conical part as in my invention) help during manufacturing the device by injecting plastic mold at the top of the handle to equally and satisfactory distribute liquid plastic through the semi conical part and rest of the body.

Regarding the semi conical part 21, it has a large opening 22 at its base at its connection to the circumferential flange and an anterior opening 27 connected to the opening 22 by a narrower slot keeping the shape and the property of the semi conical part preventing the glans from any slight protrusion and in the same time prevent accumulation of urine in this small area.

How to Use this Circumcision Device

1. After applying two hemostats to foreskin, gently separate the adhesions using either the pointed or spatula end of the probe (FIG. 7).

2. Use two hemostats to spread the foreskin and another to crush the foreskin (FIG. 8) where the dorsal slit is to be made. The foreskin should be crushed to a length that is approximately the same as the width of the glans. This can be visualized while the foreskin is being pulled and dissected.

3. Place ligature with surgeon's knot and leave loose at the base of the penis (FIG. 9).

4. With tissue scissors, make the dorsal slit along the crushed line. The slit should be no longer than necessary to permit the bell to be worked into place, and it should not exceed the length of the previously crushed area. Gently retract the foreskin and free any remaining adhesions, completely exposing sulcus (FIG. 10).

5. Place bell of appropriate size (see "Proper Size Selection FIG. 4") over the glans so it avoids undue pressure on ventral vessels. Apex of dorsal slit should be distal to bell's groove. Pull foreskin only enough to position apex of dorsal slit distal to groove (FIG. 11).

To hold bell while tying ligature, the third hemostat may be used to clamp foreskin to handle, as illustrated (FIG. 12).

6. After positioning ligature around bell's groove, draw ligature very tightly so it compresses foreskin into groove; tie with surgeon's knot. Snip off excess ligature (FIG. 13). You should be able to see an unobstructed urethral meatus.

7. Trim off foreskin using outer ridge of bell as cutting guide (FIG. 14).

8. Break off bell handle and discard it. Leaving the bell and ligature in place, you should be able to see an unobstructed urethral meatus (FIG. 15). No dressing is necessary. The rim of tissue under and distal to the ligature will become necrotic and separate with the bell in 5 to 8 days, leaving a clean, healed line of excision.

If the physician desires, the bell can be removed before the infant is sent home by cutting the ligature at the knot. This may be done after 36 to 48 hours following circumcision, based on physician's evaluation.

BRIEF DESCRIPTION OF THE DRAWINGS

FIG. 7 represents step 1 of how to use the device

FIG. 8 represent step 2 of how to use the device.

FIG. 9 represent step 3 of how to use the device.

FIG. 10 represents step 4 of how to use the device.

FIG. 11 represent step 5 of how to use the device.

FIG. 12 is how to hold the bell while tying ligature.

FIG. 13 represents step 6 of how to use the device.

FIG. 14 represents step 7 of how to use the device.

FIG. 15 represents step 8 of how to use the device.

Figure 1:
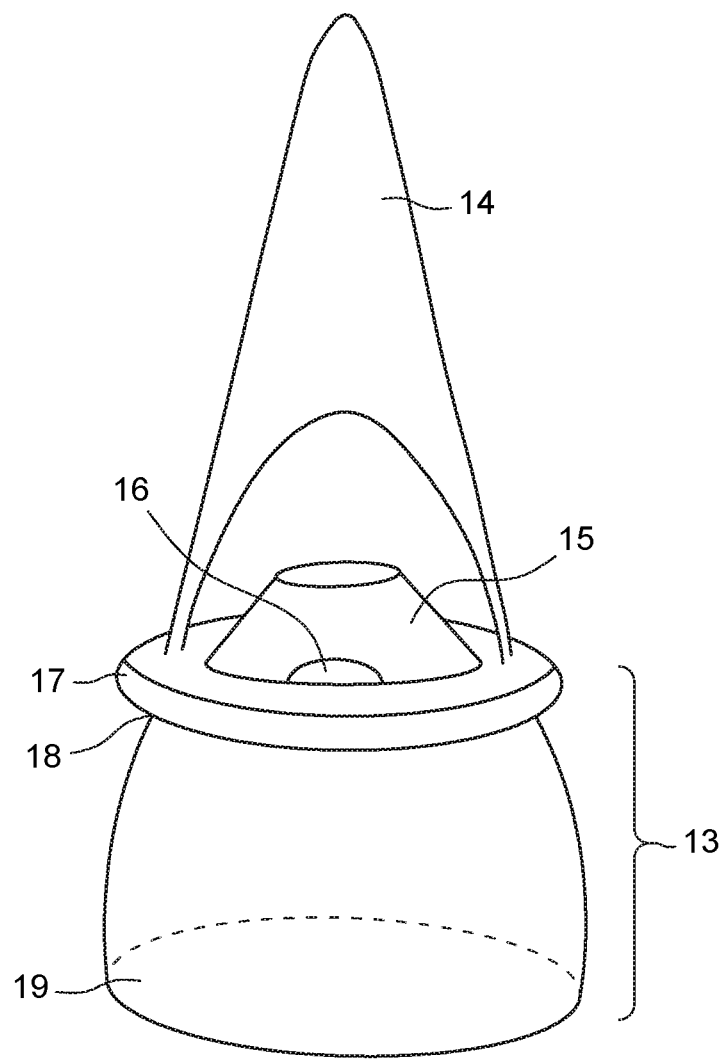
FIG. 1 is the circumcision device invented by me at 1988/17446.
Figure 2:
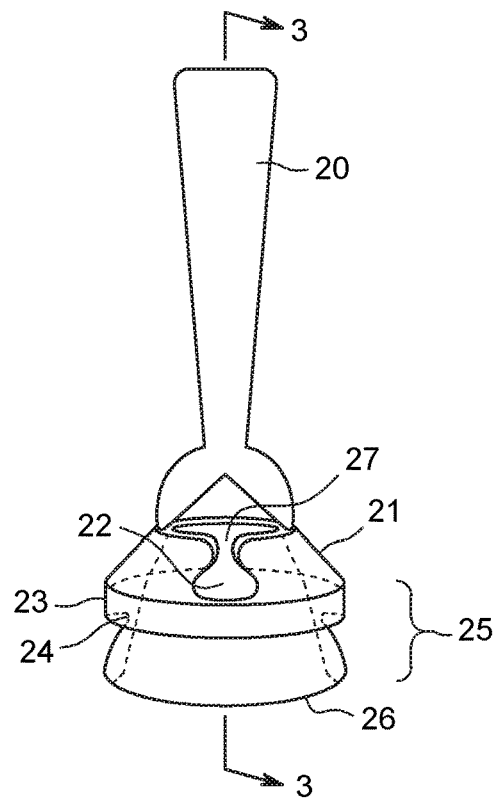
FIG. 2 is an elevational view of one embodiment of the circumcision device in accordance with this invention.
Figure 3:
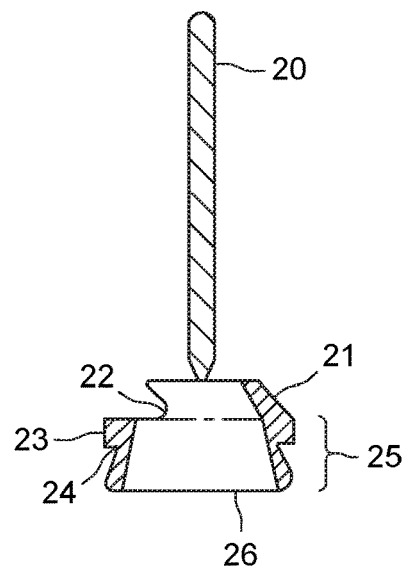
FIG. 3 is a vertical cross-sectional view of the circumcision device as viewed along line 3-3 in (FIG. 2).
Figure 4:
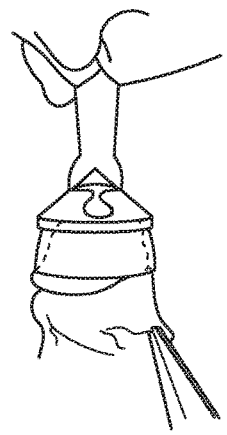
FIG. 4 represents a proper size selection of the device according to the glans size.
Figure 5:
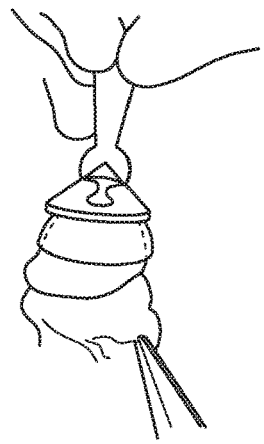
FIG. 5 when the device is smaller than the size of the glans.
Figure 6:
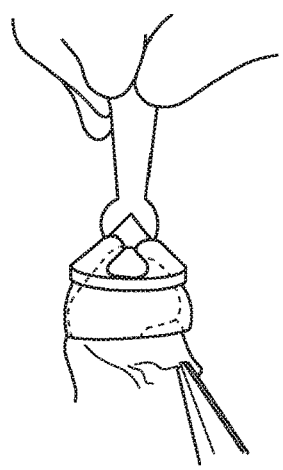
FIG. 6 when the device is larger than the size of the glans.

The invention claimed is:

1. A circumcision device that comprises:
   a hollow bell-shaped body comprising an open anterior end, an open posterior end, a circumferential flange proximal to the open anterior end on an exterior surface of the bell-shaped body;
   a semi-conical part comprising an open anterior end and an open posterior end, the open posterior end of the semi-conical part extending from the circumferential flange, wherein the open anterior end of the semi-conical part prevents slippage of the circumcision device to a shaft of a penis on which the circumcision device is configured to be mounted, when the circumcision device is mounted on the penis; and
   a handle having an inverted Y-shape comprising two forked legs, each of the two forked legs coupled to a periphery of the open anterior end of the semi-conical part, the coupling forming a junction, wherein the junction is formed structurally weak to facilitate detaching the handle from the semi-conical part at the junction.

2. The circumcision device of claim 1, wherein the semi-conical part comprises a slot on the body of the semi-conical part, the slot extending from the open anterior end of the semi-conical part towards the open posterior end of the semi conical part, wherein the slot increases in size from the open anterior end of the semi-conical part to the open posterior end of the semi-conical part.

3. The circumcision device of claim 1, further comprising a circumferential groove on the bell-shaped body, the circumferential groove located below the circumferential flange.

4. The circumcision device of claim 3, wherein the semi-conical part comprises a slot on the body of the semi-conical part, the slot extending from the open anterior end of the semi-conical part towards the open posterior end of the semi conical part, wherein the slot increases in size from the open anterior end of the semi-conical part to the open posterior end of the semi-conical part.

5. The circumcision device of claim 1, wherein the hollow bell-shaped body comprises:
   a tapered interior surface extending from the open anterior end of the bell-shaped body to the open posterior end of the bell-shaped body, wherein the open posterior end of the bell-shaped body is larger than the open anterior end of the bell-shaped body.

6. The circumcision device of claim 1, wherein the handle has a thickness of about 2 mm.

7. The circumcision device of claim 1, wherein the open anterior end of the semi-conical part has a dimension is smaller than the dimension of a glans of the penis on which the circumcision device is configured to be mounted.

* * * * *